United States Patent [19]

Manolios

[11] Patent Number: 6,057,294
[45] Date of Patent: May 2, 2000

[54] PEPTIDE

[75] Inventor: Nicholas Manolios, Kensington, Australia

[73] Assignee: Northern Sydney Area Health Service of Pacific Highway, St. Leonards, Australia

[21] Appl. No.: 08/875,013

[22] PCT Filed: Jan. 16, 1996

[86] PCT No.: PCT/AU96/00018

§ 371 Date: Sep. 15, 1997

§ 102(e) Date: Sep. 15, 1997

[87] PCT Pub. No.: WO96/22306

PCT Pub. Date: Jul. 25, 1996

[30] Foreign Application Priority Data

Jan. 16, 1995 [AU] Australia .................................. 95/0589
Jan. 16, 1995 [AU] Australia .................................. 95/0590

[51] Int. Cl.[7] .................................................. A61K 38/00
[52] U.S. Cl. .................................. 514/13; 514/14; 514/15; 514/16; 514/17; 530/326; 530/327; 530/328; 530/329; 530/330
[58] Field of Search .................................. 530/326, 327, 530/328, 329, 330; 514/13–17

[56] References Cited

U.S. PATENT DOCUMENTS 5,223,485  6/1993  Kawai et al. ............................. 514/16

FOREIGN PATENT DOCUMENTS

| 0 388 232 | 9/1990 | European Pat. Off. |
| 9009162 | 8/1990 | WIPO |
| 9119797 | 12/1991 | WIPO |
| 9212168 | 7/1992 | WIPO |
| WO 93/17699 | 9/1993 | WIPO |
| WO 94/20127 | 9/1994 | WIPO |
| WO 95/19568 | 7/1995 | WIPO |
| WO 95/25122 | 9/1995 | WIPO |
| WO 95/26980 | 10/1995 | WIPO |

OTHER PUBLICATIONS

Ching et al., "Interaction of immune sera with synthetic peptides corresponding to the structural protein region of hepatitis C virus" *PNAS* 89(8):3190:3190–3194(1992).

Cerny et al., "Cytotoxic T lymphocytes restricted by HLA–A2 specific for hepatitis C virus (HCV) derived peptides are present in the peripheral blood of patients with chronic hepatitis C" *J Cell Biochem*, "Keystone Symmposia on Molecular and Cellular Biology" SUP17D(N308):64(1993).

Cerny et al., "Cytotoxic T lymphocyte response to hepatitis C virus–derived peptides containing the HLA–A2.1 binding motif" *J Clin Invest*, 95(2):521–530(1995).

Manolios et al., "Transmembrane Helical Interactions and the Assembly of the T Cell Receptor Complex" *Science*, 249:274–277(1990).

Manolios et al., "Pairwise, cooperative and inhibitory interactions describe the assembly and probable structure of the T–cell antigen receptor" *EMBO J*, 10(7):1643–1651(1991).

Manolios et al., "The T cell antigen receptor α and β chains interact via distinct regions with CD3 chains" *Eur. J. Immunol.*, 24:84–92(1994).

Chen et al., Journal of Immunology, 152: 2874–2881,(1994).

Orlandi et al., Eur. J. Immunol., 24: 2868–2873,(1994).

CA 54:321(e), Erlanger et al., J. Am. Chem. Soc. 81, 3051–4, 1959.

HCAPLUS DN 121:298720, Orlandi et al., Eur. J. Immunol. 24(11), 2868–73 (abstract), 1994.

HCAPLUS DN 121:76418, Yu et al., Cell, 76(5), 933–45 (abstract), 1994.

HCAPLUS, DN 120:267663, Chen et al., J. Immunol., 152(6), 2874–81 (sbstract), 1994.

HCAPLUS DN 119:28584, Diaz et al., J. Am. Chem. Soc., 115(9), 3790–1 (abstract), 1993.

HCAPLUS AN 1991: 221389, Kawai et al., WO 9009162, 1990.

CAPLUS AN: 1978: 168294, Caporale et al., *Pept., Proc. Am. Pept. Symp*, 5th, 225–7. (abstract), 1977.

Harris et al., *Biochemistry*, vol. 13, No. 7, pp. 1510–1515, 1974.

Manolios et al., *Eur. J. Immunol.*, 24: 84–92, 1994.

*Primary Examiner*—Dwayne C. Jones
*Assistant Examiner*—C. Delacroix-Muirheid
*Attorney, Agent, or Firm*—Needle & Rosenberg, P.C.

[57] ABSTRACT

The present invention provides peptides which affect T-cells, presumably by action on the T-cell antigen receptor. The present invention further relates to the therapy of various inflammatory and autoimmune disease states involving the use of these peptides. Specifically, the peptides are useful in the treatment of disorders where T-cells are involved or recruited. The peptide is of the following formula: A-B-C-D-E in which: A is absent or 1 or 2 hydrophobic amino acids, B is a positively charged amino acid, C is a peptide consisting of 3 to 5 hydrophobic amino acids, D is a positively charged amino acid, and E is absent or up to 8 hydrophobic amino acids.

12 Claims, 2 Drawing Sheets

PEPTIDE

This application is a 371 of PCT/AU96/0018 filed Jan. 16, 1996.

The present invention relates to peptides which affect T-cells, presumably by action on the T-cell antigen receptor. The present invention further relates to the therapy of various inflammatory and autoimmune disease states involving the use of these peptides. Specifically, the peptides are useful in the treatment of disorders where T-cells are involved or recruited.

T-cells are a subgroup of cells which together with other immune cell types (polymorphonuclear, eosinophils, basophils, mast cells, B-, NK cells), constitute the cellular component of the immune system. Under physiological conditions T-cells function in immune surveillance and in the elimination of foreign antigen(s). However, under pathological conditions there is compelling evidence that T-cells play a major role in the causation and propagation of disease. In these disorders, breakdown of T-cell immunological tolerance, either central or peripheral, is a fundamental process in the causation of autoimmune disease.

Central tolerance involves thymic deletion of self reactive cells (negative selection) and positive selection of T-cells with low affinity for self major histocompatibility complex antigens (MHC). In contrast, there are four, non-mutually exclusive hypotheses that have been proposed to explain peripheral T-cell tolerance which are involved in the prevention of tissue specific autoimmune disease. These include: anergy (loss of co-stimulatory signals, down regulation of receptors critical for T-cell activation), deletion of reactive T-cells, ignorance of the antigen by the immune system and suppression of autoreactive T-cells. Tolerance once induced does not necessarily persist indefinitely. A breakdown in any of these mechanisms may lead to autoimmune disease.

Autoimmune disease and other T-cell mediated disorders are characterised by the recruitment of T-cells to sites of inflammation. T-cells at these sites, coupled with their ability to produce and regulate cytokines and influence B-cell function, orchestrate the immune response and shape the final clinical outcome. An understanding of the process of antigen recognition and subsequent T-cell activation, leading to T-cell proliferation and differentiation, is therefore pivotal to both health and disease. The critical component of antigen recognition on the surface of T-cells is the complex antigen receptor (TCR) which is a multisubunit structure that recognises antigen in the context of MHC-encoded proteins on the surface of antigen-presenting cells. Disturbance in this intricate structure-function relationship of the TCR, integrating antigen recognition with T-cell activation may provide the therapeutic means to deal with inflammation and T-cell mediated disorders.

The TCR is composed of at least seven transmembrane proteins. The disulfide-linked (αβ-Ti) heterodimer forms the clonotypic antigen recognition unit, while the invariant chains of CD3, consisting of ε, γ, δ, and ζ and η chains, are responsible for coupling the ligand binding to signalling pathways that result in T-cell activation and the elaboration of the cellular immune responses. Despite the gene diversity of the TCR chains, two structural features are common to all known subunits. Firstly, they are transmembrane proteins with a single transmembrane spanning domain—presumably alpha-helical. Secondly, all the TCR chains have the unusual feature of possessing a charged amino acid within the predicted transmembrane domain. The invariant chains have a single negative charge, conserved between the mouse and human, and the variant chains possess one (TCR-β) or two (TCR-α) positive charges. Listed below in TABLE 1 is the transmembrane sequence of TCR-α in a number of species showing that phylogenetically this region is highly conserved indicating an important functional role. The substitutions between species are very conservative.

TABLE 1

Sequence comparison of TCR-α transmembrane region

| SPECIES | SEQUENCE |
|---|---|
| MOUSE | NLSVMGLRILLLKVAGFNLLMTL (SEQ ID NO: 1) |
| RAT | NLSVMGLRILLLKVAGFNLLMTL (SEQ ID NO: 1) |
| SHEEP | NLSVTVFRILLLKVVGFNLLMTL (SEQ ID NO: 2) |
| COW | NLSVI VFRILLLKVVGFNLLMTL (SEQ ID NO: 3) |
| HUMAN | NLSVI GFRILLLKVAGFNLLMTL (SEQ ID NO: 4) |

Studies on the assembly of the multicomponent TCR by Manolios et al (1990, 1991, 1994) showed that the stable interaction between TCR-α and CD3-δ and TCR-α and CD3-ε was localised to eight amino acids within the transmembrane domain of TCR-α (shown above in bold) and it was the charged amino acids arginine and lysine that were critical for this process. This finding exemplified the fact that amino acids within the transmembrane domain not only functioned to anchor proteins but were important in the assembly of subunit complexes and protein-protein interactions.

The above system depended on the modification of complementary strand DNA (cDNA) to create a number of protein mutants. Chimeric cDNA molecules were transfected into COS (fibroblast line) cells to express the required protein. Coexpression of these chimeric proteins were used to evaluate the region of interaction. Reiterating the above, the technology involved cDNA manipulation, metabolic labelling, immunoprecipitation and gel electrophoresis.

Transmembrane domains are small in size and proteins transversing this region are usually constrained to an alpha-helical configuration. These biophysical features coupled with the ability to engineer protein-protein interactions via transmembrane charge groups suggested to the present inventor a possible new approach to intervene and potentially disturb TCR function.

The present inventor has developed a series of peptides that are inhibitors of function of this crucial receptor, presumably by interfering with assembly. The present inventor has also found that these peptides have an effect on T-cell mediated inflammation and that carboxyl terminal conjugation did not alter the function of the peptides. This is exemplified by coupling peptide to a lipid carrier system with increased effect and no loss of function. In addition, the present inventor has also found that the peptide alone had the ability to translocate intracellularly making it a potentially effective drug delivery system. The efficacious clinical manifestations of the administered peptide would be a decrease in inflammation, e.g. as demonstrated by a decrease of arthritis in an adjuvant model of arthritis.

Accordingly, in a first aspect the present invention consists in a peptide of the following formula:

A-B-C-D-E in which:
- A is absent or 1 or 2 hydrophobic amino acids
- B is a positively charged amino acid
- C is a peptide consisting of 3 to 5 hydrophobic amino acids
- D is a positively charged amino acid, and
- E is absent or up to 8 hydrophobic amino acids In a preferred embodiment of the present invention C is 3 or 4 hydrophobic amino acids.

In a further preferred embodiment of the present invention A is 2 hydrophobic amino acids and E is 1 to 3, and preferably 1, hydrophobic amino acids.

In yet a further embodiment of the present invention B is arginine and D is lysine or B is lysine and D is arginine.

In yet a further preferred embodiment of the present invention the peptide is Gly-Leu-Arg-Ile-Leu-Leu-Leu-Lys-Val (SEQ ID NO: 5), Leu-Lys-Ile-Leu-Leu-Leu-Arg-Val (SEQ ID NO: 6), Gly-Phe-Arg-Ile-Leu-Leu-Leu-Lys-Val (SEQ ID NO: 7) or Phe-Lys-Ile-Leu-Leu-Leu-Arg-Val (SEQ ID NO: 8).

In a second aspect the present invention consists in a therapeutic composition comprising the peptide of the first aspect of the present invention and a pharmaceutically acceptable carrier.

In a third aspect the present invention consists in a method of treating a subject suffering from a disorder in which T-cells are involved or recruited, the method comprising administering to the subject a therapeutically effective amount of the composition of the second aspect of the present invention.

The therapeutic composition may be administered by any appropriate route as will be recognised by those skilled in the art Such routes include oral, transdermal, intranasal, parenteral, intraarticular and intraocular.

In a fourth aspect the present invention consists in a method of delivering a chemical moiety to a cell comprising exposing the cell to the chemical moiety conjugated to the peptide, preferably to the carboxy terminal, as claimed in any one of claims 1 to 10.

A non-exhaustive list of disorders in which T-cells are involved/recruited include:

Allergic diathesis e.g. delayed type hypersensitivity, contact dermatitis

Autoimmune disease e.g. systemic lupus erythematosus, rheumatoid arthritis, multiple sclerosis, diabetes, Guillain-Barre syndrome, Hashimotos disease, pernicious anemia Gastroenterological conditions e.g. Inflammatory bowel disease, Crohn's disease, primary biliary cirrhosis, chronic active hepatitis Skin problems e.g. psoriasis, *pemphigus vulgaris*

Infective disease e.g. AIDS virus, herpes simplex/zoster

Respiratory conditions e.g. allergic alveolitis,

Cardiovascular problems e.g. autoimmune pericarditis

Organ transplantation

Inflammatory conditions e.g. myositis, ankylosing spondylitis.

As used herein the term "subject" is intended to cover both human and non-human animals.

As will be recognised from the above discussion the peptide of the present invention is based on a portion of transmembrane domain of TCR-α. The complete murine sequence of this portion is NLSVMGLRILLLKVAGFNLL-MTLRLWSS (SEQ ID NO: 9), whereas the corresponding human sequence is NLSVIGFRILLLKVAGFNLLMTL (SEQ ID NO: 4). There is complete sequence homology across a range of species in the last 15 amino acids of the TCR-alpha chain distal to the sequence upon the peptide of the present invention is based (shown in bold). Peptides including these additional 15 residues may have activity similar to the peptide of the present invention. The essential feature is that the peptide includes two positively charged amino acids separated by 3 to 5 hydrophobic amino acids. Further, as will be clear from the following examples, the peptide of the present invention may be modified at the carboxy terminal without loss of activity. Accordingly, it is intended that the present invention includes within its scope peptides which include additional amino acids to the "core" sequence of the peptide of the present invention and which affect the T-cell antigen receptor.

As demonstrated in the following examples the peptide of the present invention is able to enter cells. Accordingly it is envisaged that, apart from its other uses, the peptide of the present invention could be used as a "carrier" to deliver other therapeutic agents to cells. This could be achieved, for example, by conjugating the therapeutic to be delivered into the cell to the peptide of the present invention.

As will be readily understood by those slklled in this field hydrophobic amino acids are Ala, Val, Leu, Ile, Pro, Phe, Tyr and Met, whilst positively charged amino acids are Lys, Arg and His.

In order that the nature of the present invention may be more clearly understood, preferred forms thereof will now be described with reference to the following examples.

EXAMPLE 1

Synthesis of Peptide

The first step was to synthesise a short hydrophobic peptide corresponding to the predetermined assembly sequence. The amino acid sequence of the competitive peptide is $NH_2$-Gly-Leu-Arg-Ile-Leu-Leu-Leu-Lys-Val-OH (SEQ ID NO: 5) hereafter referred to as "core peptide". Subsequently a number of other peptides listed in TABLE 2 were synthesised (>95% purity, by Auspep Australia, Melbourne, Australia) and examined for their effect on T-cell function and inflammation.

TABLE 2

Peptides and their sequence

| PEPTIDE | SEQUENCE |
|---|---|
| Core peptide | Gly-Leu-Arg-Ile-Leu-Leu-Leu-Lys-Val-OH (SEQ ID NO: 5) |
| A | Met-Gly-Leu-Arg-IIe-Leu- Leu-Leu-OH (SEQ ID NO: 10) |
| B | Leu-Gly-Ile-Leu-Leu-Leu-Gly-Val-OH (SEQ ID NO: 17) |
| C | Leu-Lys-IIe-Leu-Leu-Leu-Arg-Val-OH (SEQ ID NO: 6) |
| D | Leu-Asp-Ile-Leu-Leu-Leu-Glu-Val-OH (SEQ ID NO: 12) |
| E | Leu-Arg-Ile-Leu-Leu-Leu-Ile-Lys-Val-OH (SEQ ID NO: 13) |
| F | Leu-Arg-Leu-Leu-Leu-Lys-Val-OH (SEQ ID NO: 14) |

EXAMPLE 2

Solubility

The core peptide and other peptides listed above were noted to be hydrophobic and insoluble in aqueous solutions. A variety of solvents and carriers were tested. These included ethanol, dimethylsulphoxide (DMSO), dimethyl formamide (DMF), trifluoracetic acid (TFA), squalane oil (2,6,10,15,19,23-hexamethyltetracosane), and lipid conjugation by addition of palmitic acid to the core peptide via TRIS-conjugation (Whittaker R.G., Bender V. J. 1991) to increase solubility. The preferred solvent was DMSO and the final concentration used in cell cultures ranged from 0.1%–0.2%. Concentrations of DMSO greater than 1% was toxic to cells. Stock solutions of peptide and lipopeptide conjugates were dissolved in DMSO and used in a 1/1000 dilution.

The addition of peptide/lipopeptide in DMSO to aqueous solutions resulted in "fat" or "crystal" globules that settled to the bottom of the tissue culture flask and dissolved poorly. These globules could be seen by phase contrast microscopy, but were less obvious for lipid conjugates.

Core peptide containing $C^{14}$-glycine ($C^{14}$-peptide) was synthesised by Auspep Australia and used to study solubility. $C^{14}$-peptide dissolved/suspended in DMSO was added to a final concentration of 100 $\mu$M to T-cell media (RPMI 1640 supplemented with 10% foetal calf serum and 0.3% mercaptoethanol: TCM) and shaken. The media was centrifuged and supernatant filtered through 0.2 $\mu$M filter or left unseparated. The total radioactivity in unseparated medium was 20.000 cpm, 1000 cpm after the medium was centrifuged and 500 cpm after the media was filtered. These experiments highlight the insoluble nature of the peptide in vitro and suggest that approximately 5% goes into solution.

EXAMPLE 3

Entry of Peptide into Cells

To examine if peptide enters cells, $C^{14}$-peptide was added to a flask of $5 \times 10^6$ 2B4.11 cells (T-cell hybridoma specific for cytochrome c) in a final concentration of 100 $\mu$M and 0.2% DMSO and incubated overnight. The adherent cells were washed four times with phosphate buffered saline (PBS) in the flask, solubilised with triton-containing buffer and radioactivity counted. The amount of radioactivity in the supernatant seas 70,000 cpm and 5000 cpm in the solubilised cells.

In a variation of the above experiment, 2B4.11 cells ($7.5 \times 10^4$) were grown in Petri dishes containing 2 ml of TCM and a "Transwell" with 0.4 $\mu$M membrane was placed in the Petri dish. $C^{14}$-peptide in a final concentration of 100 $\mu$M and 0.1% DMSO were added in the "Transwell" and after 24 hr and 48 hr incubation the counts determined on both sides of the filter and in the cells. Approximately 85% of radioactivity was retained in the "Transwell", 8% in the Petri dish media and 7% within cells. The above experiments demonstrated that peptide was able to enter cells. Considering the low solubility of peptide (5%–10%) all of the available peptide in solution entered the cells (7%).

EXAMPLE 4

Intracellular Localisation of Fluoresceinated Peptide in T-cells

Experiments suggested that the small percentage of peptide that goes into solution can enter/or be taken up by cells. To confirm this, core peptide covalently linked with fluorescein isothiocyanate (FITC) was added to T-cells and intracellular localisation determined by visualisation using confocal or conventional UV light microscopy.

Fluoresceinated labelled core peptide was prepared as follows: 10.25 mg of core peptide was dissolved in 0.5 ml dimethylformamide (DMF) and 2 $\mu$M of FITC in 0.5 ml of DMF was added dropwise with stirring, at room temperature. The pH was adjusted to 9 with N-methyl, N,N-diisopropylamine, and the reaction allowed to proceed for 1 hr. Semi-preparative HPLC was then used to separate FITC-peptide from free FITC, using a C-4 column (6 ml/min; buffer A, 0.1% TFA; buffer B, 80% acetonitrile, 20% water; 0.1% TFA; linear gradient of 40%–100% B). Fractions were monitored by analytical HPLC and the fractions containing pure fluoresceinated core peptide (FITC-peptide) pooled.

Two flasks of cultured 2B4.11 cells ($5 \times 10^6$) were spun down and resuspended in PBS containing calcium and magnesium. To one flask, FITC dissolved in DMSO was added to a final concentration of 10 $\mu$M and to the other FITC-peptide 10 $\mu$M. The final concentration of DMSO in both flasks was 0.1% previously shown to have no effects on T-cells. The cells were incubated at 37° C. for 30 min and then examined under the confocal microscope.

The observations can be summarised as follows: (i) FITC and FITC-peptide entered the cells; (ii) free HITC gave brighter fluorescence than FITC-peptide in the cells; (iii) the intracellular staining pattern was not different between the free FITC and FITC-peptide. Nuclear and especially bright nucleolar staining was observed; (iv) conjugation of peptide by FITC did not prevent entry of peptide into cells; (v) there was no "leaching" out of cells of FITC-peptide over a 5 hr period. These experiments demonstrate that FITC-peptide could be taken up by cells and localised intracellularly. In conjuction with experiments previously described showing intracellular uptake by $C^{14}$-peptide it is evident that it is the inherent nature of the peptide sequence and not its conjugates (FITC, $C^{14}$) that allows cellular entry.

EXAMPLE 5

Tris-fat Conjugation of Core Peptide Carboxyl Terminal

The effect of carboxyl conjugation of core peptide, as exemplified by lipid conjugation, on the ability of peptide to competitively inhibit the function of this crucial receptor was investigated. The efficacious clinical manifestations of the administered lipopeptide would be a decrease in inflammation e.g. as demonstrated by a decrease of arthritis in an adjuvant model of arthritis, as would be seen with peptide. In addition to the lipoconjugation of core peptide a number of other lipopeptides were synthesised and used as controls in subsequent experiments. The lipopeptides were synthesized according to the methods set out in Whittaker, R. G., Hayes, P. J., and Bender, V. J. (1993) Peptide Research 6, 125 and Australian Patent No. 649242. The disclosure of these references is incorporated by herein by cross reference Preparation of Fluorescein Labelled Gly-Leu-Arg-Ile-Leu-Leu-Leu-Lys-Val-Gly-Tris-mono- and tri-palmitates. To a solution of each of the deprotected lipopeptides (15 and 6 mg) in DCM (1 ml) a solution of FITC (4 mg 10 μmole) in DMF (500 μl) was added with stirring. The apparent pH of the reaction was maintained at 9.0 by the addition of triethyl amine (TEA). The fluorescein-labelled mono, and tri-palmitoyl derivative of the peptide were purified by semi-preparative HPLC (C4 column, System B). The purified compounds were evaporated to dryness and lyophilised from tert. butyalcohol to give the fluorescein labelled peptide monopalmitate ($R_t^B$, 7.83) and tripalmitate ($R_t^B$ 9.85) which were tested as described below.

TLC of the fluorescein-labelled lipopeptides (DCM: MeOH, 95:5) showed the absence of free FITC and free Gly-Tris-monoparnitate and Gly-Tris-tripalmitate (used in lipopeptide synthesis) (by ninhydrin staining).

Solid Phase Peptide Synthesis. Gly-Leu-Arg-Ile-Leu-Leu-Leu-Lys-Val (SEQ ID NO: 5) (core peptide) and its fully protected form, Boc-Gly-Leu-Arg(PMC)-Ile-Leu-Leu-Leu-Lys(Boc)-Val-OH (SEQ ID NO: 16) (and the C14 -labelled peptide) were supplied by Auspep Pty Ltd. Both were synthesised by the FMOC-chemistry in the manual mode.

It will also be readily understood by those skilled in the art that there are a number of well known linkers that can be used to join compounds (such as peptides) with a carboxyl group to an amino group. These include:

a) a linker with an amino group to the compound and a carboxyl group to the Tris (or amino acid if present) such as an amino acid or antibiotic.
b) a linker with an amino group to the compound and a sulphonic acid group to the Tris (or amino acid if present) such as 2-aminoethanesulphonic acid (taurine).
c) a linker with an hydroxyl group to the compound and a carboxyl group to the Tris (or amino acid if present) such as glycolic acid, lactic acid etc.
d) a linker with an hydroxyl group to the compound and a sulphonic acid group to the Tris (or amino acid if present) such as 2-hydroxyethanesulphonic acid (isethonic acid).
e) a linker with an hydroxyl group to the compound and a reactive halide group to the Tris (or amino acid if present) such as 2-chloroethanol.
f) other examples of potentially suitable linkers between a compound with a reactive carboxyl and the amino group of Tris (or amino acid if present) include the compound families exemplified by p-hydroxybenzaldehyde, 2-chloroacetic acid, 1,2- dibromoethane and ethyleneoxide.

Linkers could also contain disulphide groups that would reduce to liberate modified peptide intracellularly.

EXAMPLE 6

Localisation of FITC Conjugated Lipopeptides in COS Cells

Using con-focal microscopy, the ability of FITC-conjugated lipopeptides to enter non-T cells (COS cells-fibroblasts) was examined.

Materials:

Stock concentration in DMSO—Core peptide.Tris.monopalmitate. FITC (MW 1862) 10 mM; core peptide.Tris.di-palmitate.FITC (MW 2334) 10 mM; core peptide.Tris.tri-palmitate.FITC (MW 2806) 10 mM; glycine.Tris.monopalmitate.FITC (MW 805) 10 mM; glycine.Tris.tri-palmitate.FITC (MW 1286) 10 mM; FITC, (MW 390) 6.4 mM.

Method:

COS cells were grown on coverslips until 80% confluent, washed twice with PBS and incubated with FITC conjugated lipopeptides for 15 min or 2 hr. The final concentration of lipopeptides was 10 μM and 6.4 μM for FITC, for each time point respectively. Cells were washed twice with PBS, mounted with PBS/glycerol and examined with confocal microscopy.

Results:

Experiments indicated that fluorescein-conjugated lipopeptides can transmigrate across cell membranes and localise to within the cellular cytoplasm, reaching as far as the endoplasmic reticulum (ER), where protein synthesis takes place. The extent of cellular penetration was influenced by the lipid moiety attached to the peptide. Of the lipopeptides the monopaletate had the greater ability to infiltrate within the fibroblasts and T-cells so far examined (see below). The ER is the best site to try and effect assembly. Once all the chains have assembled and transported to the cell surface it may be much harder to disrupt the receptor at the cell surface membrane. Targetting peptides to the ER is an ideal site to disrupt the TCR complex.

EXAMPLE 7

Localisation of FITC Conjugated Lipopeptides in T-cells

Using con-focal microscopy, the ability of FITC conjugated lipopeptides to enter T-cells was examined.

Materials:

Lipopeptides as above. 2B4.11 T-cell hybridoma cell line.

Method:

2B4.11 T-cells were grown in TCM and resuspended in a concentration of $8 \times 10^5$ cells/ml. Viability >95% using trypan blue. One ml of cells was added to polypropylene tubes and washed twice with PBS. Cells were resuspended in PBS and one microliter of stock FITC-conjugated lipopeptides added for 30 min. Cells were washed with PBS, mounted with PBS/glycerol, and viewed using confocal microscopy.

Results:

Similar to that of COS cells (see above). Results showed that lipopeptides were able to enter T-cells. The lipoconjugation of peptide does not prevent entry of peptides into cells and has the potential use of being used as a carrier vehicle to increase solubility.

EXAMPLE 8

Effect of Peptides and Lipopeptides on TCR Assembly and Cell Surface Expression on T-cells using Flow Cytometry Analysis Materials The T-cell hybridoma 2B4.11 which expresses a complete TCR on the cell surface was used as a positive control to assess the effects of peptides on TCR expression. The cells were grown in TCM. The β-deficient variant 21.2.2 and the β- and ζ-deficient cell line 3.12.29, derived by repetitive subcloning of 2B4.11 cells (Sussman et al., 1988) and lacking TCR expression were used as negative controls.

Peptides tested included core peptide, lipopeptides and a peptide from tumor necrosis factor receptor termed 558 (used as a negative control). The final concentration of each substance used in incubation was 10 μM.

Antibodies

The following antibodies were used for immunoprecipitation and flow cytometry analysis: Mouse IgG2a monoclonal antibody (MAb) against TCR-α chain of the T-cell hybridoma 2B4 (A2B4-2, Samelson et al., 1983), MAb against 2B4.11 TCR-β chain (K)25), hamster IgG anti-CD3-ε MAb (145-2C11 [2C11], Leo et al., 1987), rabbit anti-CD3-ε polyclonal antiserum raised against purified mouse CD3-ε (127, Minami et al., 1987), anti-CD3-δ polyclonal antibody (R9) raised in goat immunized with a COOH-terminal peptide of the mouse CD3-δ chain (Samelson et al., 1986).

Method

FACS analysis: $1 \times 10^6$ (2B4.11, 21.2.2) cells were incubated with a number of separate peptides and lipopeptides in a final concentration of 10 μM overnight. The cells were then wvashed with PBS and incubated with 50 μl primary antibody (A2B4 or 2C11) for 30 mins at 4° C. Cells were washed twice in PBS and 0.1% BSA and incubated for an additional 30 min at 4° C. with FITC-labelled second antibody. Cells were washed two additional times with PBS and 0.1% BSA prior to analysis on a Becton-Dickson FACS Analyser or Becton-Dickson FACS Scan.

Results

The expression of TCR on 2B4.11 cells treated with core peptide control peptide, or lipopeptides did not alter the cell surface expression of the receptor. These experiments have been repeated with higher concentration of core peptide (100 μM) and longer incubation times ranging from 1–10 days and the results have been the same showing no change in T-cell surface antigen receptor expression.

The following experiments were performed to assess the in vitro effects of peptides/lipopeptides on T-cell function.

EXAMPLE 9

Antigen Presentation Assay I

An antigen presentation assay (described below) examined the ability of a number of peptides to inhibit T-cell activation following antigen recognition, by measuring the product of T-cell activation, Interleukin-2 (IL-2).

Material. The following cell lines were used: 2B4.11, a T-cell hybridoma that expresses a complete antigen receptor on the cell surface (Samelson et al., 1983) and produces IL-2 following antigen recognition (cytochrome c). Interleukin-2 dependent T-cell line (CTLL) for conventional biological IL-2 assays; and the B-cell hybridoma cell line LK 35.2 (LK, I-$E^k$ bearing; Kappler et al., 1982) which acts as the antigen presenting cell. The hybridomas were grown in TCM. Cytochrome c (Sigma, USA) was added in the media to give a final concentration of 50 μM in the antigen presenting assay.

Peptides examined included: core peptide, seven other control peptides from a variety of sources having an equivalent length to core peptide and peptides A, B, C, D, E and F. The final concentration of the peptides in the antigen presentation assay was examined at several levels ranging from 10 μM to 100 μM.

Method. For T-cell antigen stimulation $2 \times 10^4$ LK35.2 cells were co-cultured with 50 μM pigeon cytochrome c dissolved in PBS and $2 \times 10^4$ 2B4.11. T-cells for 16 hr. The assay was done in triplicate. Supernatants were recovered and IL-2 content determined by CTLL proliferation. The incorporation of $^3$H-thymidine is directly proportional to the amount of IL-2 present in the supernatant. The ability of different peptides to inhibit IL-2 production was examined. In addition to measuring $^3$H-thymidine incorporation, IL-2 measurements (IU/ml) were also determined.

Results. In assays where either cytochrome c (antigen) or LK cells (antigen presenting cells) were omitted there was no IL-2 production. The lack of T-cell activation under such conditions indicated that there was no lipopolysaccharide (LPS) or endotoxin in the solutions which mav have non-specifically stimulated the T-cells. The combination of all three constituents of the assay at the concentrations shown above resulted in the production of IL-2 as measured by high $^3$H-thymidine incorporation by CTLL cells (22,000 cpm). When core peptide or other analogues were added to the assay system the amount of IL-2 produced varied respectively. All peptides tested at 10 μM had no effect on IL-2 production. The best effect was noted with core peptide at 100 μM and peptide C (100 μM) leading to a 15%–30% reduction in IL-2 production compared to control. This was reproducible on at least three separate occasions. Peptides A, B, D, E and F had a variable and minor effect on T-cell activation. The seven control peptides with equivalent length but no sequence homology to the peptide had no effect on IL-2 production.

Preincubation of core peptide and other peptides at 37° C. in TCM prior to addition in the antigen presenting assay, improved solubility and activity and was reflected as an additional incremental increase above baseline activity noted with freshly prepared peptide.

EXAMPLE 10

Antigen Presentation Assay II

The following experiments were performed to assess the in vitro effects of lipopeptides on T-cell function.

Material. Lipopeptides examined included: core peptide Tris-monopalmitate (100 μM and 0.1% DMSO) and core peptide Tris-tripalmitate (100 μM and 0.2% DMSO). The final concentration of the two lipopeptides in the antigen stimulation assay is shown in brackets respectively.

Method. As described in Example 9.

Results. Initially, when core peptide Tris-tripalmitate (100 μM and 0.2% DMSO) was added, there was a reduction in T-cell activation by 75% (highest count 5.190 cpm cf 22,000 cpm for control). The addition of core peptide Tris-monopalmitate (100 μM and 0.1% DMSO) had a profound effect on IL-2 production, with only 137 cpm recorded (similar to background). The concentration of 0.1% DMSO and 0.2% DMSO used in the test system was examined and not found to influence IL-2 production. Subsequent experiments have confirmed these findings and show an IL-2 reduction of 86%–92% compared to control. Palmitic acid alone (100 μM) used to conjugate the peptide, added to the antigen presenting assay system did not affect IL-2 production.

The following experiments examined the ability of core peptide to circulate within the animal following administration, and the effects on experimentally induced inflammation.

EXAMPLE 11

Distribution of $C^{14}$-core Peptide

To examine the distribution of subcutaneously injected peptide in mice, $C^{14}$-core peptide (5 mg/mouse) was dissolved in 150 microliters of squalane oil and injected at the base of the tail of Balbic mice. After 24 hr, counts were measured from pulped organs. Distribution of the peptide was noted in thymus (5%), spleen (7%), blood (3%) and a large proportion in lymph nodes (28%), kidney (30%) and liver (28%).

Experiments were extended to examine the ability of core peptide to prevent disease in animal models of inflammation. Three in vivo experimental models including adjuvant induced arthritis in rats, cyclophosphamide induced diabetes in NOD mice, and experimental allergic neuritis in rats were used. In these models, encompassing two species, core peptide was able to influence the degree of inflammation.

EXAMPLE 12(a)

Adjuvant Induced Arthritis in Rats

The rat adjuvant arthritis model is a classic model of inflammation which has been used extensively by a number of laboratories to study disease progression and effects of potential new anti-inflaimatory drugs thereon over the last 30 years (Pearson et al., 1961; Cremer et al., 1990; Holmdahl and Kvick., 1992; Cannon et al.,1993). This model has also been widely used by researchers at the Royal North Shore Hospital over the last 10 years and procedures have been established for the study of this model of inflammation. All procedures on the animals were carried out under halothane/oxygen/nitrous oxide anaesthesia (2% v/v halothane in 1 liter/min $O_2$ and 2 liters/min$N_2O$). Rats were injected intradermally at the base of the tail with a minimal adjuvant dose (1 mg heat killed *Mycobacterium tuberculosis* [MTB9 in 100 μl squalane) once and only once. The method for coadmainistrating test samples with MTB was first described by Whitehouse et al., 1990. At regular intervals between days 0–28, animals were weighed and their arthritic condition assessed by measurement of maximum tail thickness and rear paw thickness (with a micrometer screw gauge). Rats were housed in holding bins after the initial tail injection and allowed access to unlimited water and pellet food. On day 29 the animals were sacrificed.

Materials. The first experiment consisted of 12 rats weighing approximately 190–210 grams that were purchased from the Perth Animal Resource Centre (ARC) and maintained in the Gore Hill Animal House facility. Used were core peptide (30 mg) suspended in adjuvant (0.6 ml squalane containing 7 mg MTB), core peptide Tris-monopalmitate (15 mg) suspended in 0.6 ml adjuvant, core peptide Tris-tripalmitate 20 mg/0.6 ml of adjuvant.

Rats were divided into four groups, each group containing three rats. First group received adjuvant only (positive control), second group adjuvant with core peptide, third group core peptide.Tris. monopalmitate suspended in adjuvant, and last group core peptide.Tris. tripalmitate in adjuvant. Rats were injected with the above compounds in a 0.1 ml volume at the base of the tail. Baseline measurements of rat weight, paw width, and tail diameter were made on Day 0, and subsequently on day 4, 7, 9, 14, 16, 18, 21, 25 and 28. Arthritis was graded and animals sacrificed if there was marked swelling, redness and obvious discomfort. Not all rats given MTB developed arthritis. In general more than 80% of control rats developed arthritis.

Results. After 18 days all the control animals given adjuvant only had developed arthritis and had to be sacrificed. Two of the three core peptide treated animals (2/3) had no evidence of arthritis. Similarly, two of the three animals given core peptide.Tris.tripalmnitate had no evidence of arthritis. Animals given core peptide.Tris.monopalmitate and adjuvant all developed arthritis. However, the onset and development of arthritis in this latter group was prolonged by 3–4 days and the clinical severity was much reduced (number of joints, paw swelling, loss of weight) compared to controls.

Experiments using adjuvant induced arthritis in rats showed that the peptide and its lipid conjugate had a protective effect on the induction of arthritis in this animal model. Results of repeat and subsequent experiments using a number of different peptides (7 mg/rat) and drugs are summarised in TABLE 3.

TABLE 3

Effects of different peptides on adjuvant induced arthritis in rats.

| PEPTIDE | INDUCTION OF ARTHRITIS | | EFFECT |
|---|---|---|---|
| | MTB ALONE | WITH PEPTIDE | |
| CORE | 3/3 (100%) | 1/3 (33%) | Protective |
| | 3/5 (60%) | 1/5 (20%) | Protective |
| | 5/5 (100%) | 1/4 (25%) | Protective |
| A | 2/4 (50%) | 4/6 (67%) | Protective |
| B | 2/4 (50%) | 2/4 (50%) | No effect |
| C | 4/5 (80%) | 0/4 (0%) | Protective |
| D | 4/5 (80%) | 4/5 (80%) | No effect |
| E | 5/5 (100%) | 3/5 (60%) | Protective |
| F | 5/5 (100%) | 0/5 (0%) | Protective |
| CS* | 5/5 (100%) | 1/5 (20%) | Protective |
| DXM* | 5/5 (100%) | 4/4 (100%) | No effect+ |

CS*, cyclosporin, 50 mg/kg; DXM, dexamethasone (2 mg/kg).
+, animals developed arthritis but the onset of arthritis was delayed by 3–4 days.

The results of the above experiments indicated that core peptide had an effect on inflammation both to delay its onset, decrease severity, and prevent onset of disease. These effects were similar to those obtained with the co-administration of cyclosporin and adjuvant. Cyclosporin is a well known and widely used immunosuppressive agent. There was no indiscriminate effect of peptide action. Best results were noted with core peptide, peptide C and F. Core peptide and peptide C each have charged amino acid groups at the same site but the amino acids reversed. This indicated that it was the charge group rather than the particular amino acid that was important. In contrast there was no effect noted with peptide B or D having either no or negative charge group amino acids respectively. Extending the amino acids downstream towards the carboxy terminus had no negative effect. This observation confirms that carboxy modification can be performed without loss of biological activity. Therefore these peptides can be used as carrier peptides for the delivery of other chemical moieties. Increasing the amino acid number between the two polar charge groups (peptide E) resulted in lower efficacy. Decreasing the number of amino acids between the charged groups (peptide F) had no negative effect.

EXAMPLE 12(b)

Dosage Effect of Core Peptide

Based on previous experiments by Whitehouse et al (personal communication) an initial dose of 5–7 mg/rat was given. To evaluate a lower limit, a number of different core peptide concentrations were examined. The results (TABLE 4) indicated that in addition to a specific action of core peptide it was limited by its effects by dosage.

TABLE 4

Effect of core peptide dosage on adjuvant induced arthritis.

| | INDUCTION OF ARTHRITIS | | |
|---|---|---|---|
| PEPTIDE | MTB ALONE | WITH PEPTIDE | EFFECT OF PEPTIDE |
| 7 mg | 11/13 (85%) | 3/12 (25%) | Protective |
| 3.5 mg | 4/5 (80%) | 2/5 (40%) | Protective |
| 1.7 mg | 6/7 86%) | 7/8 (88%) | No effect |

EXAMPLE 12(c)

Tail Diameter Measurements

A feature of adjuvant induced arthritis is the development of inflammation in the tail. Tail measurements (mm) between saline injected rats and core peptide treated rats were not statistically significant. Tail diameters from MTB treated rats however were significantly increased (p<0.001) compared to saline and core peptide treated rats (p<0.001), TABLE 5.

TABLE 5

Effect of core peptide on tail inflammation as assessed by tail thickness (mm)

| | DAY | | | | | |
|---|---|---|---|---|---|---|
| TREATMENT | 0 | 5 | 10 | 15 | 20 | 25 |
| SALINE (n = 4) | 7.13 | 7.75 | 7.95 | 8.48 | 8.78 | 8.80 |
| MTB only (n = 5) | 6.86 | 8.80 | 8.96 | 9.46 | 9.60 | 9.73 |
| MTB + PEPTIDE (n = 5) | 7.23 | 7.62 | 8.24 | 8.76 | 8.96 | 9.10 |

In addition to the oedema noted in the tails, MTB alone given to rats caused ulceration and inflammation at the site of injection that was not present with rats given core peptide or saline.

EXAMPLE 13

Experimental Allergic Neuritis (EAN)

To further confirm the ability of core peptide to delay and diminish the severity of disease induced by T-cells a different model (experimental allergic neuritis) was tested "blind" by independent experimenters (Associate Professor Pollard and Mr J Taylor) at a different institution (University of Sydney).

Materials and Methods

Animals. Male Lewis rats weighing between 239–451 grams were obtained from the Bosch Animal House, University of Sydney colony or from ARC, Perth. All experiments were conducted in accordance with experimental guidelines approved by the Animal Care and Ethics Committee of the University of Sydney.

Induction of EAN. Lewis rats were immunised in each hind footpad with 50–75 $\mu$l of bovine peripheral nerve myelin (PNM) emulsified in complete Freunds adjuvant. The immunisation emulsion consisted of equal volumes of saline and incomplete Freunds adjuvant (Sigma, USA) mixed with bovine PNM and MTB (strain H37RA, DIFCO) added at 15 mg/ml and 5 mg/ml respectively. Where animals received ovalbumin/peptide the peptide was added to the immnmnisation emulsion at 70 mg/ml. These experiments were performed with the experimenters having no knowledge of what peptide was in the immunisation emulsion.

Animals were observed at least every second day post immunisation for clinical signs and were scored using the following scale: 0, normal; 0.5, weak tail; 1, flaccid tail; 1.5, limp tail and ataxia in hind legs; 2, paraparesis; 2.5, limp tail and severe paraparesis; 3, paraplegia; 3.5, limp tail and paraplegia and forelimb paresis; 4, quadraparesis; 4.5 limp tail and quadraplegia; 5, dead.

Peripheral Nerve Myelin Isolation. Bovine PNM was prepared essentially as described by Norton and Podulso (1973).

Results.

Figure 1A:
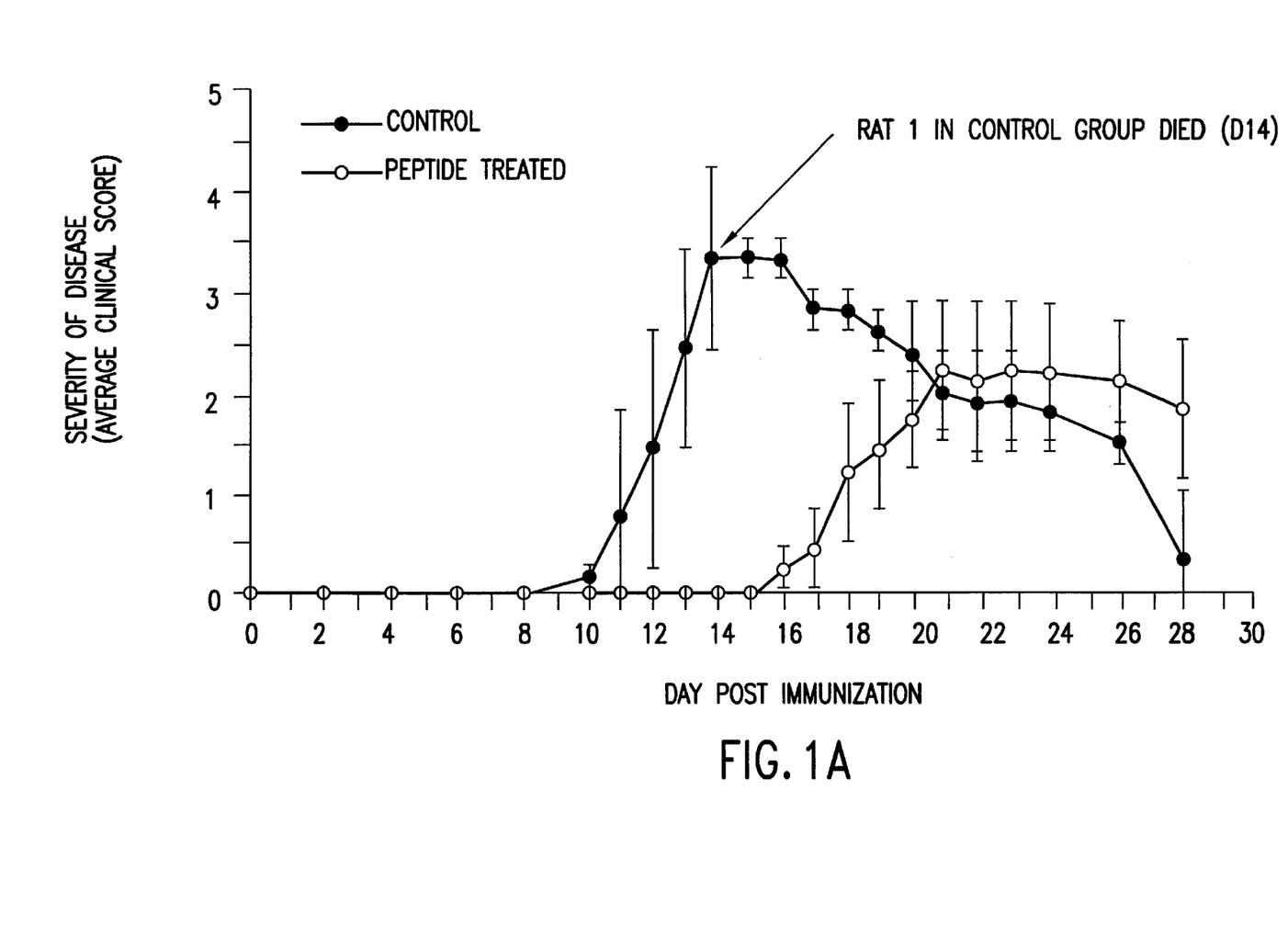
FIG. 1A shows the delayed induction and clinical severity of disease in animals treated or untreated with the core peptide.
Figure 1B:
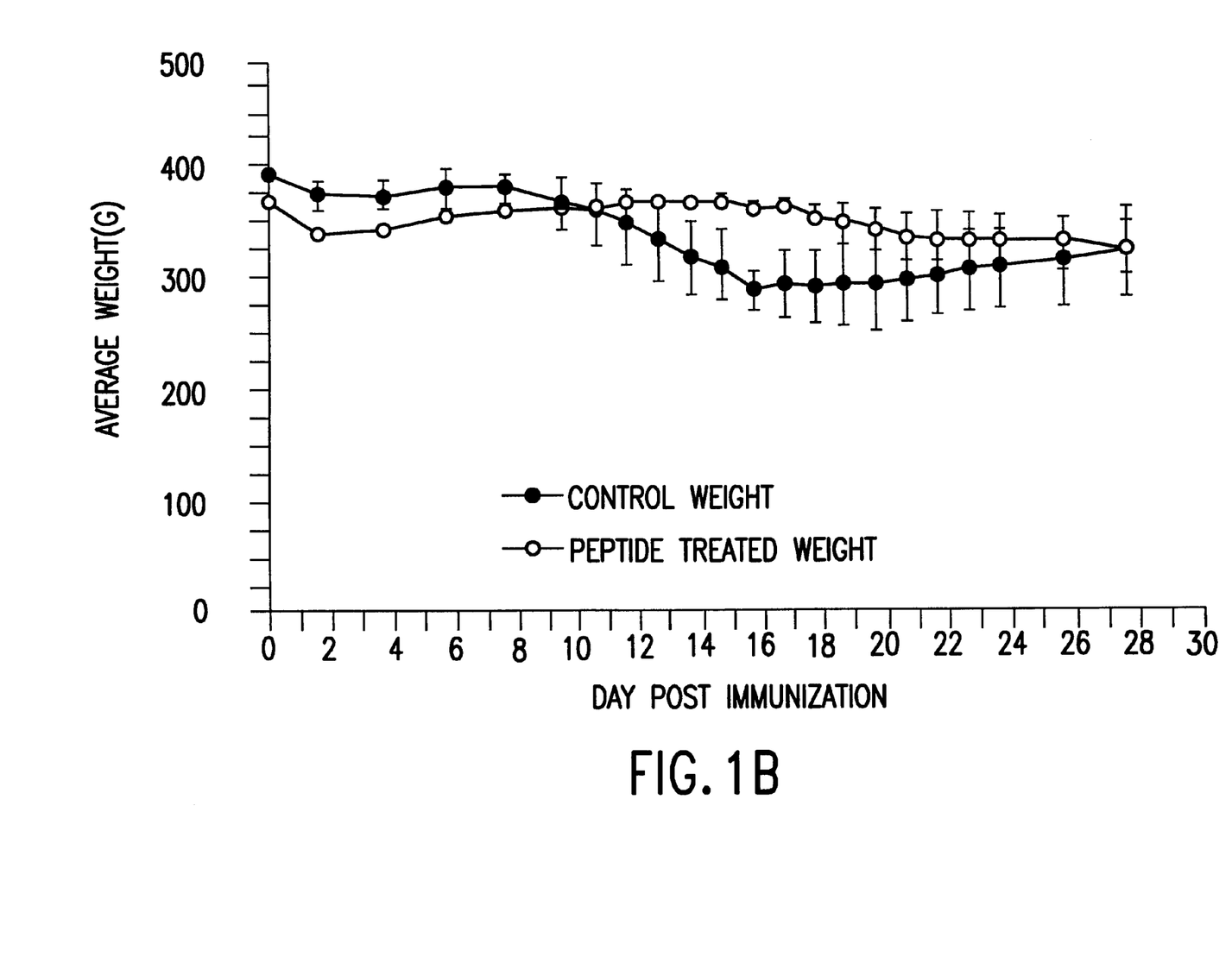
FIG. 1B shows the average weight of animals treated or untreated with the core peptide.

A representative example is shown in FIG. 1. In this experiment core peptide delayed induction and clinical severity of disease. Similar data were observed for peptide C. These data confirm the efficacy of core peptide and peptide C as general immunosuppressants.

EXAMPLE 14

Diabetes in NOD/Lt (F) Mice

In yet another model of T-cell mediated disease the effects of subcutaneously injected core peptide on the induction of diabetes in NOD/Lt (F) mice was tested "blind" by an independent experimenter (Prof L Harrison, WEHI, Melbourne).

A cellular autoimmune process that selectively destroys the pancreatic islet beta cells is thought to be responsible for the development of insulin-dependent diabetes mellitus (IDDM) in humans and in the spontaneous animal models including the NOD mouse (Leiter et al., 1987). A common histopathological feature associated with the development of IDDM is insulitis, the presence within and around the islets of mononuclear cells consisting predominantly of T lymphocytes and to a lesser extent macrophages (Foulis et al., 1986). Experimental strategies aimed at suppressing cellular autoimmunity such as neonatal thymectomy, administration of cyclosporin A or administration of anti-T lymphocyte antibodies prevent the development of diabetes (Campbell et al., 1991).

Animals

NOD/Lt(F) mice 10 weeks old at experimental Day 0. This is a high-incidence strain commonly used as an animal model for diabetes.

Materials

Core peptide dissolved in squalane at a stock concentration of 3.33 mg/ml. Ovalbumin used as a control was suspended in squalane at a stock concentration of 3.33 mg/ml. Peptide and ovalbumin were "solubilised" just prior to injection, with vortexing. A total of 250 μg (75 μl) was injected subcutaneously on the right flank on Day −1, 0 and 1. Mice were given intraperitoneal cyclophosphamide in water at 300 mg/kg on Day 0. Blood glucose measurements were taken on Day 0, 10, 14 and 21. There were 16 mice in the treatment group and 16 in the ovalbumin control group.

Results. Experiments demonstrate a protective effect of core peptide on the induction of autoim-mune beta cell destruction which manifests as diabetes (TABLE 6). This finding again confirms the general immunosuppressive ability of core peptide in a different T-cell mediated disease model.

TABLE 6

Effects of core peptide on the induction of diabetes in NOD/Lt (F) mice

| TREATMENT | PERCENTAGE OF MICE DEVELOPING DIABETES | | | |
|---|---|---|---|---|
| | DAY 0 | DAY 10 | DAY 14 | DAY 21 |
| Ovalbumin (n = 16) | 0% | 0% | 42% | 65% |
| Peptide (n = 16) | 0% | 0% | 5% | 12% |

Summary

In recent years a vast number of different methods have been used and devised to interfere with the interaction between TCR, MHC or antigen (trimolecular complex) and thereby influence immune responses. The therapeutic potential associated with the development of these ideas and methods of application has not been overlooked. The strategies have included the use of monoclonal antibodies to block MHC or TCR interactions, bloclkng antibodies to important co-stimulatory or regulatory proteins on the T-cell surface, vaccination with disease inducing T-cells, or TCR epitopes, competing antigens, and inhibition of cytokines or their receptors. The ability to disrupt TCR function by a specific competitive peptide designed to affect assembly has not been previously reported and examined. The present inventor has clearly shown that the peptides of the present invention are able to inhibit T-cell mediated immune responses in at least three different models by a mechanism previously unreported.

The experiments described herein were principally conducted with a core peptide deliberately chosen to be homologous with the known sequence of the mouse and rat TCR alpha chain. However, for clinical treatment of humans a peptide containing a phenylalanine residue instead of leucine towards the amino terminus of the core peptide may be preferable to maximise homology with the known human sequence (TABLE 1).

It will be appreciated by persons sldlled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Bansal et al. (1993). Curr Ther Res 54:1
Bevins C. L., Zasloff M. (1990). Am Rev Biochem. 59, 395
Campbell, I. L., Kay, T., Oxbrow, L., Harrison, L. (1991). J.Clin.Invest87, 739.
Cannon et al. (1993) Arthritis and Rheum. 36:126
Clevers H., Alarcon B., Wileman T., Terhorst C. (1988). Am Rev. Immunol. 6,629
Cosson P., Lankford S. P., Bonifacino J. S., Klausner R., (1991). Nature 351, 414
Cremer et al. (1990). Clin Exp Immunol 82:307
DeGrado W. F., Musso G. F., Lieber M., Kaiser E. T., Kezdy F. J. (1982). Biophys J. 37, 329
Foulis, A., Liddle, C. N., Farquharson, M., Richmond, J. (1986). Diabetologia. 29, 267.
Francis et al. (1989). Arthritis and Rheum. 32:608.
Hart et al. (1993). Eur. J. Immunol. 23:1588
Hashida et al. (1991). Agents Actions 34:242.
Higashijima T., Uzu S., Nakajima T., Ross E. M. (1988). J. Biol Chem 263, 6491
Holmdahl R and Kvick. (1992). Clin Exp Immunol 88:96
James J. A. and Harley J. B. (1992). J. Immunol. 148, 1074
Kappler J., White J., Wegmann E., Mustain E., Marrack P. (1982) PNAS79, 3604
Leiter, E., Prochaska M., Coleman, D. (1987). Amer. J. Pathol. 128, 380–393.
Manolios N., Bonifacino J. S., Klausner R. D., (1990) Science, 248, 274
Manolios N., Letourner F., Bonifacino J. S., Klausner R. D. (1991) EMBO J. 10, 1643
Manolios N. (1992). Todays Life Sciences 4,32
Manolios N., Kemp, O., Li. ZG (1994). Eur. J. Immunol. 24–89
Pearson et al. (1961). J Exp. Med 113.485
Samelson L. E., Germain R. N., Schwartz R. W., (1983). Proc Natl Acad.Sci U.S.A. 80,6971
Takagi et al. (1987). Pathology. 19:294
Whitehouse et al. (1990). Agents actions. 31:47
Whittaker, R. G., Bender V. J. (1991). Proceedings of the Second International Conference on Solid Phase Synthesis and Related Technologies, Canterbury, UK, August 1991 (Patent Entitled "Amino Acids, Peptides or Derivatives Thereof Coupled to Fats" filed in Australia December 1990. PCT/AU90/00599).
Whittaker, R. G., Hayes, P. J., and Bender, V. J. (1993) Peptide Research 6, 125 and Australian Patent No. 649242.
Zhang et al. (1990). J. Immunol 145:2489

I claim:

1. A therapeutic composition comprising a pharmaceutically acceptable carrier and a peptide of the following formula:

A-B-C-D-E in which:
- A is absent, or glycine and 1 hydrophobic amino acid, or 1 or 2 hydrophobic amino acids
- B is a positively charged amino acid
- C is a peptide consisting of 4 hydrophobic amino acids
- D is a positively charged amino acid, and
- E is 1 to 8 hydrophobic amino acids, wherein the peptide is not ARLPVLKLV, RVMAPRALL or VKLFPVKLFP.

2. A therapeutic composition as claimed in claim 1 in which A is 2 hydrophobic amino acids.

3. A therapeutic composition as claimed in claim 1 in which E is 1 to 3 hydrophobic amino acids.

4. A therapeutic composition as claimed in claim 3 in which E is 1 hydrophobic amino acid.

5. A therapeutic composition as claimed in claim 1 in which B is arginine and D is lysine or B is lysine and D is arginine.

6. A method of treating a subject suffering from a disorder in which T-cells are involved or recruited, the method comprising administering to the subject a therapeutically effective amount of the therapeutic composition as claimed in claim 1.

7. A peptide in which the peptide is Gly-Leu-Arg-Ile-Leu-Leu-Leu-Lys-Val (SEQ ID NO:5).

8. A peptide in which the peptide is Gly-Phe-Arg-Ile-Leu-Leu-Leu-Lys-Val (SEQ ID NO:7).

9. A peptide in which the peptide is Leu-Lys-Ile-Leu-Leu-Leu-Arg-Val (SEQ ID NO:6).

10. A peptide in which the peptide is Phe-Lys-Ile-Leu-Leu-Leu-Arg-Val (SEQ ID NO:8).

11. A method of inhibiting T-cell function in a subject, comprising administering to the subject an amount effective to inhibit T-cell function of a peptide of the following formula:

A-B-C-D-E in which:
- A is absent, or glycine and 1 hydrophobic amino acid, or 1 or 2 hydrophobic amino acids
- B is a positively charged amino acid
- C is a peptide consisting of 4 hydrophobic amino acids
- D is a positively charged amino acid, and
- E is absent or up to 8 hydrophobic amino acids.

12. A method of delivering a chemical moiety to a cell, comprising exposing the cell to the chemical moiety conjugated to a peptide of the following formula:

A-B-C-D-E in which:
- A is absent, or glycine and 1 hydrophobic amino acid, or 1 or 2 hydrophobic amino acids
- B is a positively charged amino acid
- C is a peptide consisting of 4 hydrophobic amino acids
- D is a positively charged amino acid, and
- E is absent or up to 8 hydrophobic amino acids.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:

(A) LENGTH: 23 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:1:

Asn Leu Ser Val Met Gly Leu Arg Ile Leu Leu Leu Lys Val Ala Gly
1               5                   10                  15

Phe Asn Leu Leu Met Thr Leu
            20

(2) INFORMATION FOR SEQ ID NO:2:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:2:

Asn Leu Ser Val Thr Val Phe Arg Ile Leu Leu Leu Lys Val Val Gly
1               5                   10                  15

Phe Asn Leu Leu Met Thr Leu
            20

(2) INFORMATION FOR SEQ ID NO:3:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:3:

Asn Leu Ser Val Ile Val Phe Arg Ile Leu Leu Leu Lys Val Val Gly
1               5                   10                  15

Phe Asn Leu Leu Met Thr Leu
            20

(2) INFORMATION FOR SEQ ID NO:4:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Asn Leu Ser Val Ile Gly Phe Arg Ile Leu Leu Leu Lys Val Ala Gly
1               5                   10                  15

Phe Asn Leu Leu Met Thr Leu
            20

(2) INFORMATION FOR SEQ ID NO:5:

(i) SEQUENCE CHARACTERISTICS:
            (A) LENGTH: 9 amino acids
            (B) TYPE: amino acid
            (C) STRANDEDNESS: single (D) TOPOLOGY: linear (ii) MOLECULE TYPE: peptide (xi) SEQUENCE DESCRIPTION: SEQ ID NO:5:

Gly Leu Arg Ile Leu Leu Leu Lys Val
 1               5

(2) INFORMATION FOR SEQ ID NO:6:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Leu Lys Ile Leu Leu Leu Arg Val
 1               5

(2) INFORMATION FOR SEQ ID NO:7:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:7:

Gly Phe Arg Ile Leu Leu Leu Lys Val
 1               5

(2) INFORMATION FOR SEQ ID NO:8:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:8:

Phe Lys Ile Leu Leu Leu Arg Val
 1               5

(2) INFORMATION FOR SEQ ID NO:9:

(i) SEQUENCE CHARACTERISTICS:
            (A) LENGTH: 28 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Asn Leu Ser Val Met Gly Leu Arg Ile Leu Leu Leu Lys Val Ala Gly
 1               5                  10                  15

Phe Asn Leu Leu Met Thr Leu Arg Leu Trp Ser Ser
                 20                  25

(2) INFORMATION FOR SEQ ID NO:10:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Met Gly Leu Arg Ile Leu Leu Leu
 1               5

(2) INFORMATION FOR SEQ ID NO:11:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Leu Gly Ile Leu Leu Leu Gly Val
 1               5

(2) INFORMATION FOR SEQ ID NO:12:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Leu Asp Ile Leu Leu Leu Glu Val
 1               5

(2) INFORMATION FOR SEQ ID NO:13:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Leu Arg Ile Leu Leu Leu Ile Lys Val
 1               5

(2) INFORMATION FOR SEQ ID NO:14:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:14:

Leu Arg Leu Leu Leu Lys Val
 1               5

(2) INFORMATION FOR SEQ ID NO:15:

```
        (i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:15:

Gly Leu Arg Ile Leu Leu Leu Lys Val Gly
 1           5                       10

(2) INFORMATION FOR SEQ ID NO:16:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1
            (D) OTHER INFORMATION: Gly = "Boc-Gly"
            (A) NAME/KEY: Other
            (B) LOCATION: 3
            (D) OTHER INFORMATION: Arg = "Arg[PMC]"
            (A) NAME/KEY: Other
            (B) LOCATION: 8
            (D) OTHER INFORMATION: Lys = "Lys[Boc]"

(xi) SEQUENCE DESCRIPTION: SEQ ID NO:16:

Gly Leu Arg Ile Leu Leu Leu Lys Val
 1           5
```